United States Patent
Akiyoshi

(10) Patent No.: US 9,708,952 B2
(45) Date of Patent: Jul. 18, 2017

(54) DIAGNOSTIC DEVICE FOR UREA WATER SUPPLY SYSTEM

(71) Applicant: Hino Motors, Ltd., Tokyo (JP)

(72) Inventor: Toshiya Akiyoshi, Hino (JP)

(73) Assignee: HINO MOTORS, LTD., Tokyo (JP)

( * ) Notice: Subject to any disclaimer, the term of this patent is extended or adjusted under 35 U.S.C. 154(b) by 112 days.

(21) Appl. No.: 14/785,973

(22) PCT Filed: Jun. 11, 2014

(86) PCT No.: PCT/JP2014/065423
§ 371 (c)(1),
(2) Date: Oct. 21, 2015

(87) PCT Pub. No.: WO2014/203776
PCT Pub. Date: Dec. 24, 2014

(65) Prior Publication Data
US 2016/0076423 A1    Mar. 17, 2016

(30) Foreign Application Priority Data

Jun. 17, 2013   (JP) ................................. 2013-126774

(51) Int. Cl.
*G01N 33/00*    (2006.01)
*F01N 3/20*    (2006.01)
(Continued)

(52) U.S. Cl.
CPC ............ *F01N 3/2066* (2013.01); *F01N 11/00* (2013.01); *G01N 33/0037* (2013.01);
(Continued)

(58) Field of Classification Search
CPC ... Y02T 10/47; F01N 3/2066; F01N 2550/05; F01N 11/00; F01N 2610/02;
(Continued)

(56) References Cited

U.S. PATENT DOCUMENTS

| 7,788,902 B2 * | 9/2010 | Tsumagari ......... B01D 53/9409 60/277 |
| 8,132,402 B2 * | 3/2012 | Toshioka ............... B01D 53/90 60/277 |

(Continued)

FOREIGN PATENT DOCUMENTS

| EP | 3009622 A1 | 4/2016 |
| JP | 2002371831 A | 12/2002 |

(Continued)

OTHER PUBLICATIONS

Translation of International Preliminary Report on Patentability dated Dec. 22, 2015 corresponding to PCT/JP2014/065423, four pages.

(Continued)

*Primary Examiner* — Freddie Kirkland, III
(74) *Attorney, Agent, or Firm* — Kilpatrick Townsend & Stockton LLP

(57) ABSTRACT

A diagnostic device for a urea water supply system having a sensor for detecting a concentration of urea water includes an acquisition section that acquires a detected value of the sensor, a calculation section that calculates a NOx purification rate η by a selective reduction catalyst, and a diagnosis section that diagnoses a state of the urea water supply system. The diagnosis section is adapted to diagnose that the sensor is abnormal when only one of a first condition and a second condition is satisfied. The first condition is that the purification rate η calculated by the calculation section is greater than or equal to a reference purification rate. The second condition is that the detected value Cur acquired by the acquisition section is greater than or equal to a reference concentration.

5 Claims, 1 Drawing Sheet

(51) Int. Cl.
*F01N 11/00* (2006.01)
*B01D 53/94* (2006.01)

(52) U.S. Cl.
CPC ...... *B01D 53/9418* (2013.01); *B01D 53/9495* (2013.01); *B01D 2251/2067* (2013.01); *F01N 2550/05* (2013.01); *F01N 2560/026* (2013.01); *F01N 2560/14* (2013.01); *F01N 2610/02* (2013.01); *F01N 2900/1621* (2013.01); *Y02T 10/47* (2013.01)

(58) Field of Classification Search
CPC ........... F01N 2560/026; F01N 2560/14; F01N 2900/1621; G01N 33/0037
See application file for complete search history.

(56) References Cited

U.S. PATENT DOCUMENTS

| | | | | |
|---|---|---|---|---|
| 8,505,371 B2* | 8/2013 | Zimmerman | ......... | F02D 41/222 73/114.69 |
| 8,746,030 B2* | 6/2014 | Kasahara | ............. | F01N 3/2066 374/1 |
| 9,228,923 B2* | 1/2016 | Zimmerman | ......... | F02D 41/222 |
| 9,322,316 B2* | 4/2016 | Jung | ........................ | F01N 11/00 |
| 2008/0092522 A1* | 4/2008 | Tsumagari | ......... | B01D 53/9409 60/274 |
| 2009/0301059 A1* | 12/2009 | Toshioka | ............... | B01D 53/90 60/277 |
| 2011/0107812 A1* | 5/2011 | Kasahara | ............... | F01N 3/2066 73/1.02 |

FOREIGN PATENT DOCUMENTS

| | | |
|---|---|---|
| JP | 2006037770 A | 2/2006 |
| JP | 2008274765 A | 11/2008 |
| JP | 2010007568 A | 1/2010 |
| JP | 2010163923 A | 7/2010 |

OTHER PUBLICATIONS

European Search Report corresponding to PCT/JP2014/065423 dated Oct. 24, 2016.

International Search Report dated Aug. 25, 2014 corresponding to PCT/JP2014/065423, 4 pages.

* cited by examiner

DIAGNOSTIC DEVICE FOR UREA WATER SUPPLY SYSTEM

TECHNICAL FIELD

The techniques of the present disclosure relate to a diagnostic device for a urea water supply system. The diagnostic device diagnoses the state of the urea water supply system, which includes a sensor for detecting the concentration of urea water.

BACKGROUND ART

A conventional exhaust gas purifier is known to purify nitrogen oxide (hereinafter, refer to as NOx) in exhaust gas. The exhaust gas purifier includes a urea water supply system, which supplies urea water to the exhaust gas, and a selective reduction catalyst, into which the exhaust gas supplied with the urea water flows. For example, when water in the urea water is excessively evaporated, or when a tank is filled with fluid that does not meet standards, an abnormality occurs in the quality of the urea water. Variation in the quality of the urea water changes the amount of urea water necessary for obtaining desired purification performance in the exhaust gas purifier. On this account, the technique disclosed in Patent Document 1 causes a sensor to detect the concentration of the urea water in the tank, and suitability of the urea water is determined based on the detected value. The driver is warned when an abnormality occurs in the quality of the urea water.

PRIOR ART DOCUMENT

Patent Document

Patent Document 1: Japanese Laid-Open Patent Publication No. 2002-371831

SUMMARY OF THE INVENTION

Problem that the Invention is to Solve

To determine suitability of the urea water based on the detected value of the sensor, a required premise is that the sensor functions normally to output a valid detected value, that is, the detected value of the sensor is valid. When the detected value of the sensor is invalid, an abnormality may be determined in normal urea water, or normality may be determined in abnormal urea water. After all, the state of the urea water supply system, which includes the urea water and the sensor, is diagnosed based on only a detected value of one sensor. Thus, the diagnosis result of the state of the urea water supply system may include a false determination.

It is an objective of the technique of the present disclosure to provide a diagnostic device for a urea water supply system capable of increasing accuracy of a diagnosis result of the state of the urea water supply system.

Means for Solving the Problems

One aspect of the present disclosure is to provide a diagnostic device for a urea water supply system having a sensor for detecting a concentration of urea water. The diagnostic device comprises an acquisition section that acquires a detected value of the sensor, a calculation section that calculates a NOx purification rate by a selective reduction catalyst, and a diagnosis section that diagnoses a state of the urea water supply system. The diagnosis section is adapted to diagnose that the sensor is abnormal when only one of a first condition and a second condition is satisfied. The first condition is that the purification rate calculated by the calculation section is greater than or equal to a reference purification rate. The second condition is that the detected value acquired by the acquisition section is greater than or equal to a reference concentration.

EMBODIMENTS OF THE INVENTION

A diagnostic device for a urea water supply system according to one embodiment of the present disclosure will now be described with reference to FIGS. 1 and 2.

Figure 1:
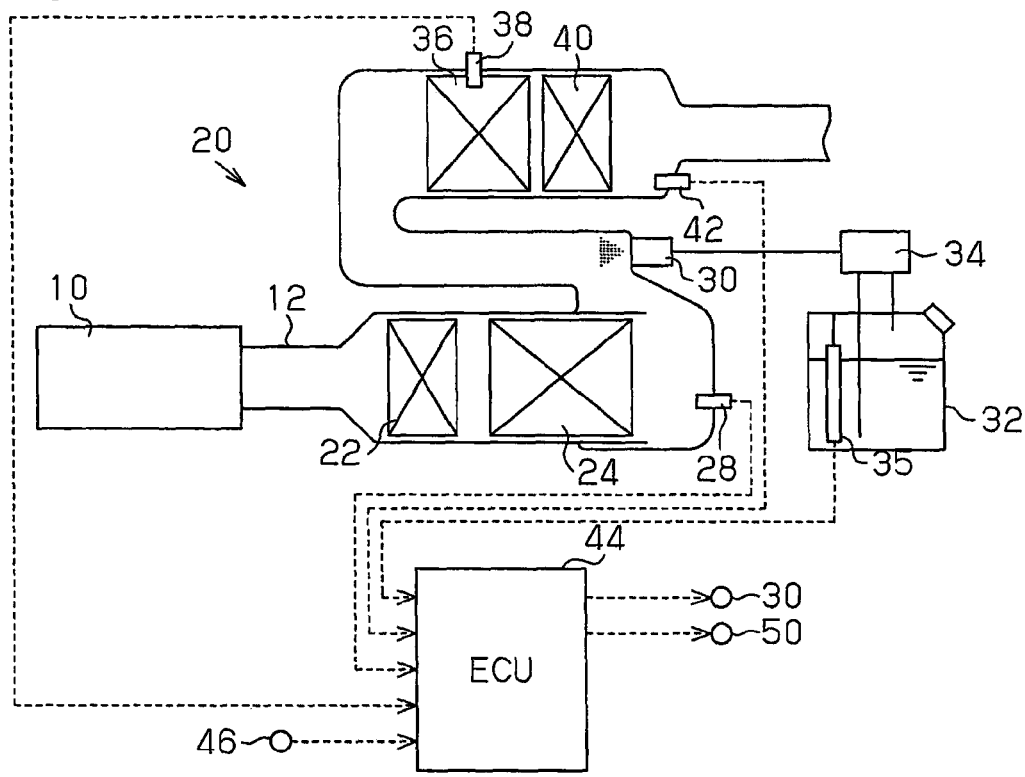
FIG. 1 is a schematic view of an exhaust gas purifier including a diagnostic device for a urea water supply system according one embodiment of the technique of the present disclosure.

As shown in FIG. 1, an exhaust gas purifier 20 for purifying exhaust gas is arranged in an exhaust passage 12 of a diesel engine 10 (hereinafter, referred to as simply "the engine 10"). Exhaust gas that has flowed into the exhaust gas purifier 20 flows into a first stage oxidation catalyst 22.

The first stage oxidation catalyst 22 is a diesel oxidation catalyst (DOC), which oxidizes and transforms hydrocarbons (HC), carbon monoxide (CO), and nitric monoxide (NO) contained in the exhaust gas into water, carbon dioxide, nitrogen dioxide, and the like. The first stage oxidation catalyst 22 includes, for example, a support, which is formed of alumina, silica, zeolite, and metal, such as platinum and palladium, and metal oxide, which are supported by the support.

The exhaust gas that has passed through the first stage oxidation catalyst 22 flows into a diesel particulate filter (DPF) 24. The DPF 24 is formed of ceramics and a metal porous body to capture particulate matter (PM) in the exhaust gas. In a regeneration process of the DPF 24, the temperature of the exhaust gas flowing into the DPF 24 is raised. This is realized, for example, by supplying combustion gas from a burner (not shown) to a portion of the exhaust passage 12 that is located upstream of the first stage oxidation catalyst 22, or by supplying fuel from a fuel injection valve (not shown) to the portion.

An upstream NOx sensor 28 as a first NOx sensor is arranged downstream of the DPF 24 and upstream of a selective reduction catalyst 36, which will be described below. The upstream NOx sensor 28 detects the NOx concentration Cnx1 of the exhaust gas that has passed through the DPF 24 at a predetermined control period. A signal indicative of a NOx concentration Cnx1, which is the detected value of the NOx sensor 28, is output to an ECU 44.

An electronically controlled injector 30 is arranged downstream of the upstream NOx sensor 28 and supplies urea water to the exhaust passage 12. A pressure pump 34 pumps urea water stored in a tank 32 to the injector 30. A relief valve (not shown) is built in the pressure pump 34 so that the urea water in the tank 32 is pumped to the injector 30 at a predetermined pressure. The ECU 44 controls opening and closing of the injector 30. The urea water supplied to the exhaust gas is hydrolyzed to ammonia with heat of the exhaust gas.

A urea water quality sensor 35 (hereinafter, referred to as simply "the sensor 35") is arranged in the tank 32. The sensor 35 detects the concentration of the urea water based on the propagation velocity of an ultrasonic wave in the urea water and the temperature of the urea water, and outputs a signal indicative of a urea water concentration Cur, which is the detected value of the sensor 35, to the ECU 44. The urea water supply system is formed with the injector 30, the tank 32, the pressure pump 34, the sensor 35, and the urea water.

A selective reduction catalyst 36 is arranged downstream of the injector 30. The selective reduction catalyst 36 performs selective catalytic reduction to reduce NOx using ammonia. The selective reduction catalyst 36 includes, for example, a support, which is formed of honeycomb ceramics, and high adsorptive zeolite or zirconia, which is supported by the support. NOx in the exhaust gas reacts with ammonia in catalysis of the selective reduction catalyst 36 and is reduced into nitrogen and water.

A catalyst temperature sensor 38 is arranged in the selective reduction catalyst 36. The catalyst temperature sensor 38 detects a catalyst temperature Ts, which is the temperature of the selective reduction catalyst 36, at a predetermined control period and outputs a signal indicative of the catalyst temperature Ts, which is the detected value of the catalyst temperature sensor 38, to the ECU 44.

The exhaust gas that has passed through the selective reduction catalyst 36 flows into the second stage oxidation catalyst 40. The second stage oxidation catalyst 40 is an ammonia slip catalyst (ASC), which dissolves ammonia unconsumed in the reduction reaction of the selective reduction catalyst 36. The second stage oxidation catalyst 40 includes, for example, a support, which includes alumina, silica, and zeolite, metal, such as platinum and palladium, and metal oxide, which are supported by the support.

A downstream NOx sensor 42 as a second NOx sensor is arranged downstream of the second stage oxidation catalyst 40. The downstream NOx sensor 42 detects a NOx concentration Cnx2 of the exhaust gas that has passed through the second stage oxidation catalyst 40 at a predetermined control period and outputs a signal indicative of the NOx concentration Cnx2, which is the detected value of the downstream NOx sensor 42, to the ECU 44.

The ECU 44 is a microcomputer, which includes a CPU, a RAM, a ROM, and the like. As described above, the ECU 44 receives signals indicative of the catalyst temperature Ts, the urea water concentration Cur, the NOx concentration Cnx1, and the NOx concentration Cnx2. In addition, the ECU 44 receives a signal indicative of an intake air amount Ga from an air flow meter 46 at a predetermined control period. The ECU 44 uses the intake air amount Ga as an exhaust gas flow amount, which is a flow amount of the exhaust gas in the exhaust passage 12. In other words, the ECU 44 functions as an acquisition section that acquires the catalyst temperature Ts, the urea water concentration Cur, the NOx concentration Cnx1, the NOx concentration Cnx2, and the intake air amount Ga.

The ECU 44 carries out various computations and processes based on information input by each of the sensors, and a control program and various types of data, which are stored in the ROM in advance. The ECU 44 controls opening and closing of the injector 30 to carry out a supply process of urea water. The ECU 44, as a diagnosis section, carries out a diagnostic process to diagnose the state of the urea water supply system, and determines the suitability of the sensor 35 and the suitability of the urea water in the tank 32. When determining that the sensor 35 or the urea water is "abnormal" in the diagnostic process, the ECU 44 activates an alarm 50 to notify the driver of the one of the sensor 35 and the urea water that is determined as "abnormal".

The ECU 44, in the supply process, calculates a supply amount of urea water at a predetermined control period. Based on the assumption that the urea water stored in the tank 32 has a desired concentration (e.g., 32.5% wt), the ECU 44 calculates a supply amount of urea water. In particular, based on the intake air amount Ga, the NOx concentration Cnx1, and the catalyst temperature Ts, the ECU 44 calculates a basic supply amount of urea water, which is an amount necessary for purifying NOx in the exhaust gas. The ECU 44 calculates a corrected supply amount of the urea water by correcting the basic supply amount based on a NOx purification rate $\eta$ ($\eta$=Cnx1/Cnx2) that is calculated from the NOx concentration Cnx1, which is the NOx concentration of the upstream NOx sensor 28, and the NOx concentration Cnx2, which is the NOx concentration of the downstream NOx sensor 42. The ECU 44 outputs a control signal to the injector 30 to supply the calculated, corrected supply amount of urea water to the exhaust gas.

The diagnostic process, which the ECU 44 carries out, will now be described with reference to FIG. 2. This diagnostic process is repeatedly carried out.

Figure 2:
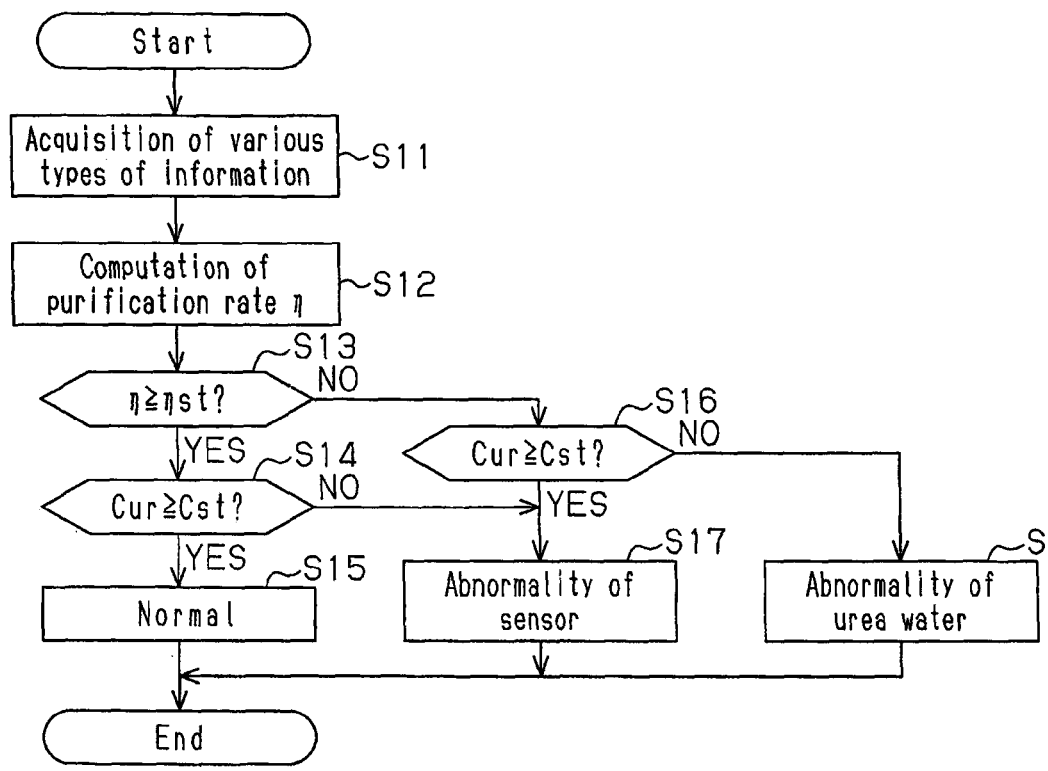
FIG. 2 is a flowchart illustrating a diagnostic process in the diagnostic device of FIG. 1.

As shown in FIG. 2, the ECU 44 at the first step S11 acquires various types of information of the concentration Cnx1, the NOx concentration Cnx2, and the urea water concentration Cur. The ECU 44, which functions as a calculation section, calculates a NOx purification rate $\eta$ based on the NOx concentration Cnx1 and the NOx concentration Cnx2 acquired at step S11 (step S12).

At the next step S13, the ECU 44 determines whether the purification rate $\eta$ is greater than or equal to a reference purification rate $\eta$st. The reference purification rate $\eta$st is a value that is preset in the various types of data. The reference purification rate $\eta$st is a purification rate at which it is determined that NOx in the exhaust gas is purified. Here, a first condition is defined as a condition that the purification rate $\eta$ is greater than or equal to $\eta$st.

When the purification rate $\eta$ is greater than or equal to the reference purification rate $\eta$st, that is, when the first condition is satisfied (step S13:YES), the ECU 44 determines whether the urea water concentration Cur acquired at step S11 is greater than or equal to a reference concentration Cst (step S14). The reference concentration Cst is a value that is preset in the various types of data. The reference concentration Cst is a concentration of urea water at which at least the reference purification rate $\eta$st is obtained by supplying a supply amount of urea water to the exhaust gas, where the supply amount is calculated in the supply process. Here, a second condition is defined as a condition that the urea water concentration Cur is greater than equal to the reference concentration Cst.

When the urea water concentration Cur is greater than or equal to the reference concentration Cst, that is, when the second condition is satisfied (step S14: YES), the ECU 44 determines that the sensor 35 and the urea water are both "normal". The ECU 44 obtains a diagnostic result of "normal" (step S15) and finishes the current diagnostic process. In contrast, when the urea water concentration Cur is less than the reference concentration Cst at step S14, that is, when the second condition is not satisfied (step S14: NO), the ECU 44 determines that the urea water is "normal" and the sensor 35 is "abnormal". The ECU 44 obtains a diagnostic result, "the abnormality of the sensor 35" at step S14 (step S17) and finishes the current diagnostic process.

When the purification rate η is less than the reference purification rate ηst at step S13, that is, when the first condition is not satisfied (step S13: NO), the ECU 44 determines whether the urea water concentration Cur acquired at step S11 is greater than or equal to the reference concentration Cst in a similar manner to step S14 (step S16).

When the urea water concentration Cur is greater than or equal to the reference concentration Cst, that is, when the second condition is satisfied (step S16: YES), the ECU 44 moves to a process at step S17. The ECU 44 determines that the urea water is "normal" and the sensor 35 is "abnormal". The ECU 44 obtains a diagnostic result, "the abnormality of the sensor 35" and finishes the current diagnostic process. In contrast, when the urea water concentration Cur is less than the reference concentration Cst, that is, when the second condition is not satisfied (step S16: NO), the ECU 44 determines that the urea water is "abnormal" and the sensor 35 is "normal". The ECU 44 obtains a diagnostic result, "the abnormality of the urea water" (step S18) and finishes the current diagnostic process. After the diagnostic process is finished, the ECU 44 activates the alarm 50 according to the diagnostic result of the diagnostic process. The driver is notified of the one of the sensor 35 and the urea water that is determined as "abnormal".

Operation of the diagnostic process will now be described.

The ECU 44 has the first condition and the second condition. The first condition is that the purification rate η is greater than or equal to the reference purification rate ηst. The second condition is that the urea water concentration Cur is greater than or equal to the reference concentration Cst. When only one of the first condition and the second condition is satisfied, the ECU 44 determines that the sensor 35 is "abnormal".

When the first condition is not satisfied but the second condition is satisfied, the purification rate η is less than the reference purification rate list even though the urea water concentration Cur is greater than or equal to the reference concentration Cst. Thus, the urea water concentration Cur of the sensor 35 should indicate a higher value than the actual concentration. In contrast, when the first condition is satisfied but the second condition is not satisfied, the purification rate η is greater than or equal to the reference purification ηst even though the concentration of the urea water is less than the reference concentration Cst. Thus, the urea water concentration Cur of the sensor 35 should indicate a lower value than the actual concentration. The suitability of the sensor 35 is determined by setting the first condition and the second condition as above.

The diagnostic device for a urea water supply system according to the above embodiment achieves the following advantages.

(1) In the diagnostic process, the suitability of the sensor 35 is determined. This increases the accuracy of a diagnostic result of the state of the urea supply system in comparison to when the suitability of the urea water is determined without determining the suitability of the sensor 35.

(2) When the first condition and the second condition are both not satisfied, the purification rate η is less than the reference purification rate ηst, and the urea water concentration Cur is less than the reference concentration Cst. In such a case, the quality of the urea water, not the sensor 35, should be abnormal. In other words, by setting the first condition and the second condition as above, not only the suitability of the sensor 35 but also the suitability of the urea water is obtained as a diagnostic result.

(3) The NOx purification rate η is calculated based on the NOx concentration Cnx1, which is a detected value of the upstream NOx sensor, and the NOx concentration Cnx2, which is a detected value of the downstream NOx sensor. In other words, the purification rate η is calculated based on the actual detected values, which directly relate to NOx. For this reason, in comparison to a case in which the purification rate η is calculated, e.g., using a value estimated based on the operation state of the engine, the reliability of the purification rate η is improved. As a result, the reliability of the diagnostic result of the diagnostic process is also improved.

The above-illustrated embodiment may be carried out in modified manners listed below.

The purification rate η may be calculated, e.g., using a value estimated according to the operation state of the engine 10.

In the diagnostic process, the suitability of the urea water does not need to be determined. In other words, only the suitability of the sensor 35 may be determined. At this time, the suitability of the urea water may be determined in a process different from the diagnostic process.

A condition for determining that the sensor 35 is "abnormal" may include a case in which only one of the first condition and the second condition is satisfied. Another condition that is different from the first condition and the second condition may be included. For example, such a condition may be that the urea water concentration Cur is less than an upper limit concentration that is greater than the reference concentration.

When the first condition and the second condition are both satisfied, or when the first condition and the second condition are both not satisfied, a determination section does not necessarily need to determine the suitability of the sensor 35.

The urea water concentration Cur may be used as a concentration of the urea water when a supply amount of the urea water is calculated in the supply process.

The engine is not limited to a diesel engine. The engine may be a gasoline engine or a natural gas engine.

The invention claimed is:

1. A diagnostic device for a urea water supply system having a sensor for detecting a concentration of urea water, the diagnostic device comprising:
    an acquisition section that acquires a detected value of the sensor;
    a calculation section that calculates a NOx purification rate by a selective reduction catalyst; and
    a diagnosis section that diagnoses a state of the urea water supply system, wherein
    the diagnosis section is adapted to diagnose that the sensor is abnormal when only one of a first condition and a second condition is satisfied, where the first condition is that the purification rate calculated by the calculation section is greater than or equal to a reference purification rate, and the second condition is that the detected value acquired by the acquisition section is greater than or equal to a reference concentration.

2. The diagnostic device for a urea water supply system according to claim 1, wherein the diagnosis section is further adapted to diagnose that the sensor is normal when the first condition and the second condition are satisfied.

3. The diagnostic device for a urea water supply system according to claim 1, wherein the diagnosis section is further adapted to diagnose that the sensor is normal when the first condition and the second condition are not satisfied.

4. The diagnostic device for a urea water supply system according to claim 1, wherein the diagnosis section is further adapted to diagnose that the urea water is abnormal when the first condition and the second condition are not satisfied.

5. The diagnostic device for a urea water supply system according to claim 1, wherein
- a first NOx sensor detects NOx concentration of exhaust gas located upstream of the selective reduction catalyst,
- a second NOx sensor detects NOx concentration of exhaust gas located downstream of the selective reduction catalyst,
- the acquisition section acquires a detected value of the first NOx sensor and a detected value of the second NOx sensor, and
- the calculation section calculates the purification rate based on the detected value of the first NOx sensor and the detected value of the second NOx sensor.

* * * * *